(12) United States Patent
Govari et al.

(10) Patent No.: US 11,903,639 B2
(45) Date of Patent: Feb. 20, 2024

(54) FLEXIBLE DISTAL-END ASSEMBLY WITH DOUBLE-SIDED ELECTRODE ARRAY AND IRRIGATION

(71) Applicant: Biosense Webster (Israel) Ltd., Yokneam (IL)

(72) Inventors: Assaf Govari, Haifa (IL); Christopher Thomas Beeckler, Brea, CA (US); Andres Claudio Altmann, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 734 days.

(21) Appl. No.: 16/852,165

(22) Filed: Apr. 17, 2020

(65) Prior Publication Data

US 2021/0322093 A1   Oct. 21, 2021

(51) Int. Cl.
*A61B 18/14* (2006.01)
*A61B 17/00* (2006.01)
*A61B 18/00* (2006.01)

(52) U.S. Cl.
CPC ............ *A61B 18/1492* (2013.01); *A61B 2017/00526* (2013.01); *A61B 2017/00867* (2013.01); *A61B 2018/0016* (2013.01); *A61B 2018/00023* (2013.01); *A61B 2018/00029* (2013.01); *A61B 2018/00214* (2013.01); *A61B 2018/00267* (2013.01); *A61B 2018/00351* (2013.01); *A61B 2018/00577* (2013.01); *A61B 2018/00613* (2013.01); *A61B 2018/1467* (2013.01); *A61B 2218/002* (2013.01); *A61B 2562/046* (2013.01); *A61B 2562/164* (2013.01)

(58) Field of Classification Search
CPC .. A61B 2018/0016; A61B 2018/00214; A61B 2218/002; A61B 2562/164; A61B 2562/046; A61B 2562/166
See application file for complete search history.

(56) References Cited

U.S. PATENT DOCUMENTS

| | | | | |
|---|---|---|---|---|
| 5,010,895 A | * | 4/1991 | Maurer | A61N 1/0524 607/138 |
| 5,846,196 A | * | 12/1998 | Siekmeyer | A61B 5/6853 606/41 |
| 9,119,533 B2 | | 9/2015 | Ghaffari | |
| 9,867,978 B1 | | 1/2018 | Rapoport et al. | |
| 2009/0306659 A1 | * | 12/2009 | Buysse | A61B 18/14 606/50 |

(Continued)

FOREIGN PATENT DOCUMENTS

| WO | WO 1996/012439 | 5/1995 |
|---|---|---|
| WO | 2021/053460 A2 | 3/2021 |

OTHER PUBLICATIONS

Extended European Search Report dated Sep. 1, 2021, from corresponding EP Application No. 21168846.0.

*Primary Examiner* — Jaymi E Della
(74) *Attorney, Agent, or Firm* — Troutman Pepper Hamilton Sanders LLP

(57) ABSTRACT

A medical probe includes a shaft and an expandable flexible distal-end assembly. The shaft is configured for insertion into a cavity of organ of a patient. The expandable flexible distal-end assembly, which is fitted at a distal-end of the shaft, includes a flat flexible backing sheet, including irrigation channels, and two flexible substrates having respective arrays of electrodes disposed thereon, the substrates attached one on either side of the backing sheet.

6 Claims, 3 Drawing Sheets

(56) References Cited

U.S. PATENT DOCUMENTS

| | | | |
|---|---|---|---|
| 2012/0172697 A1* | 7/2012 | Urman | A61B 5/062 600/374 |
| 2014/0039290 A1* | 2/2014 | De Graff | H01L 27/14632 600/377 |
| 2015/0351652 A1* | 12/2015 | Marecki | A61B 18/1492 29/829 |
| 2016/0228061 A1* | 8/2016 | Källbäck | A61B 5/0215 |
| 2017/0112405 A1* | 4/2017 | Sterrett | A61B 5/287 |
| 2018/0353753 A1 | 12/2018 | Vetter et al. | |
| 2019/0314083 A1 | 10/2019 | Herrera et al. | |
| 2019/0328274 A1 | 10/2019 | Gliner et al. | |
| 2019/0336205 A1* | 11/2019 | Highsmith | A61B 18/12 |
| 2020/0129128 A1 | 4/2020 | Gliner et al. | |

\* cited by examiner

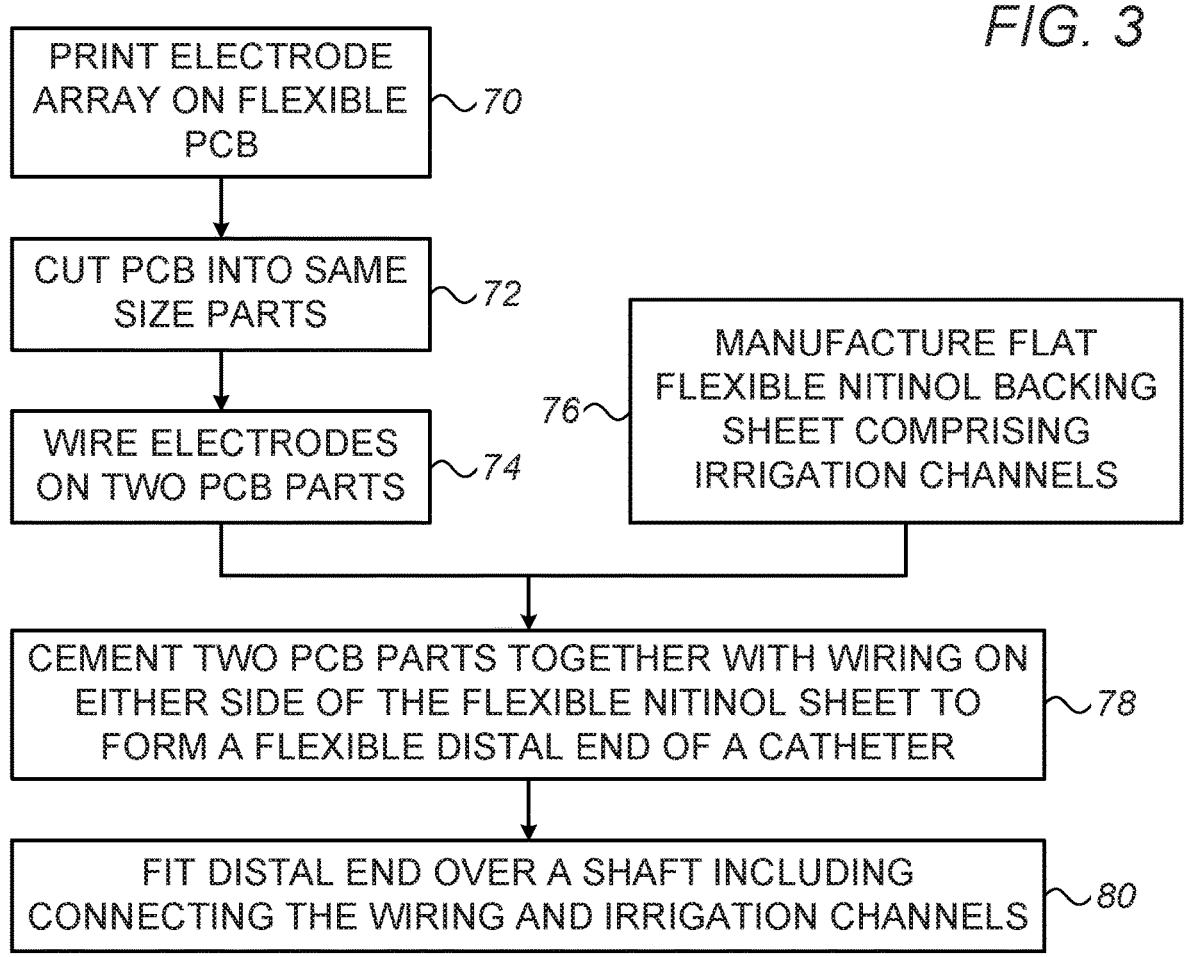

FLEXIBLE DISTAL-END ASSEMBLY WITH DOUBLE-SIDED ELECTRODE ARRAY AND IRRIGATION

FIELD OF THE INVENTION

The present invention relates generally to medical probes, and particularly to multi-electrode catheters.

BACKGROUND OF THE INVENTION

Various medical probes with multiple electrodes disposed over their distal-end were proposed in the patent literature. For example, U.S. Pat. No. 9,867,978 describes an array of electrodes on a flexible scaffolding, with the ability to collapse into an axial configuration suitable for deploying through a narrow cylindrical channel. The electrode arrays can be placed into the ventricular system of the brain, constituting a minimally invasive platform for precise spatial and temporal localization of electrical activity within the brain, and precise electrical stimulation of brain tissue, to diagnose and restore function in conditions caused by abnormal electrical activity in the brain.

As another example, U.S. Pat. No. 9,119,533 describes system, devices and methods that integrate stretchable or flexible circuitry, including arrays of active devices for enhanced sensing, diagnostic, and therapeutic capabilities. The invention enables conformal sensing contact with tissues of interest, such as the inner wall of a lumen, the brain, or the surface of the heart. Such direct, conformal contact increases accuracy of measurement and delivery of therapy. Further, the invention enables the incorporation of both sensing and therapeutic devices on the same substrate allowing for faster treatment of diseased tissue and fewer devices to perform the same procedure.

SUMMARY OF THE INVENTION

An embodiment of the present invention that is described hereinafter provide a medical probe including a shaft and an expandable flexible distal-end assembly. The shaft is configured for insertion into a cavity of organ of a patient. The expandable flexible distal-end assembly, which is fitted at a distal-end of the shaft, includes a flat flexible backing sheet, including irrigation channels, and two flexible substrates having respective arrays of electrodes disposed thereon, the substrates attached one on either side of the backing sheet.

In some embodiments, the irrigation channels are in fluid communication with surrounding blood.

In some embodiments, the substrates have openings formed therein, for flowing coolant from the irrigation channels into the surrounding blood. In other embodiments, the irrigation channels are configured to flow a coolant in a closed loop.

In an embodiment, the flexible substrates are printed circuit boards (PCBs).

In some embodiments, at least one of the electrodes is configured to be interchangeably used as an ablation electrode or as a sensing electrode.

In an embodiment, the flat flexible backing sheet includes Nitinol.

In another embodiment, the distal-end assembly is rectangular.

There is additionally provided, in accordance with another embodiment of the present invention, a manufacturing method of a medical probe, the method including preparing a flat flexible backing sheet, including irrigation channels. Two flexible substrates are fabricated, that have respective arrays of electrodes disposed thereon. The flexible substrates are attached one on either side of the backing sheet to form an expandable flexible distal-end assembly. The expandable flexible distal-end assembly is fitted at a distal-end of a shaft for insertion into a cavity of organ of a patient.

In some embodiments, fitting the distal-end assembly includes connecting the irrigation channels to a tube running in the shaft.

The present invention will be more fully understood from the following detailed description of the embodiments thereof, taken together with the drawings in which:

BRIEF DESCRIPTION OF THE DRAWINGS

FIG. 3 is a flow chart that schematically illustrates a method for manufacturing the flexible distal-end assembly of FIG. 2, in accordance with an embodiment of the present invention.

DETAILED DESCRIPTION OF EMBODIMENTS

Overview

Figure 1:
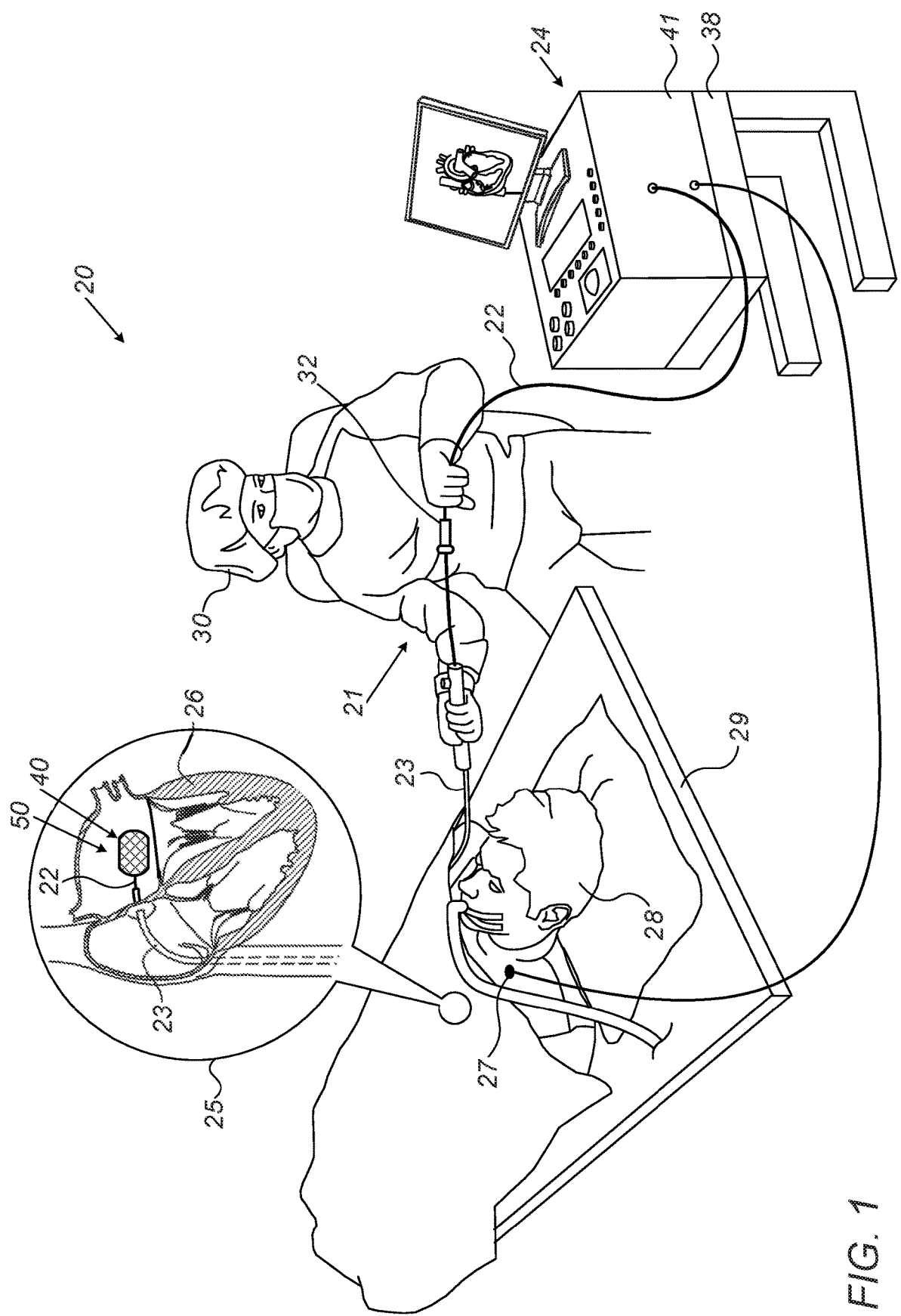
FIG. 1 is a schematic, pictorial illustration of a catheter-based cardiac diagnostic and ablation system comprising a double-sided electrode catheter, in accordance with an embodiment of the present invention.

An expandable distal-end assembly of a probe, such as of a catheter disposed with multiple electrodes for insertion into a cavity of an organ of a patient, may be employed in various clinical applications, such as electro-anatomical mapping and ablation of the cavity walls. The expandable distal-end assembly is coupled to the distal end of a shaft of the catheter, and, in a typical procedure, the catheter is inserted into the cavity (e.g., into a cardiac chamber of a heart) through a sheath with the distal-end assembly in a collapsed configuration. After exiting the sheath inside the heart, the distal-end assembly assumes its expanded configuration.

In acquiring diagnostic electro-potentials from an inner surface of the heart chamber, the electrodes disposed over the distal-end assembly need to be positioned to contact the wall surface of the chamber. Moreover, as many electrodes as possible should be simultaneously positioned in contact with the surface in order to reduce the time taken for the acquisition, and, optionally, to identify propagation directions of electro-potentials. In cases where far-field potentials are to be measured, it is advantageous to have reference electrodes close to, but not touching, tissue, while the acquiring electrodes are in contact with tissue. Such reference electrodes can be used, for example, to subtract unrelated far-field potentials from the diagnostic electro-potentials.

In the present context, a far-field bio-electric signal comes from a region distant from the contacted tissue region. Typically, such far-field bio-electric signals propagate by conduction through blood, and are sensed both by the electrodes in contact with tissue (which, in parallel, sense a "near-field signal") and by the reference electrodes.

Furthermore, when tissue ablation of a heart chamber is required, the electrodes used for the ablation need to be positioned in contact with the surface. Using multiple electrodes that are simultaneously positioned in close proximity one to the other, and also in contact with the surface, can increase the effectiveness of the ablation.

For example, in an irreversible electroporation (IRE) ablation mode, this configuration increases the strength of an applied electric field, and, optionally, locally controls a direction of the electric field to achieve better selectivity to irreversibly electroporating cardiac cells only.

While basket catheters and balloon catheters, among others, may have multiple disposed electrodes that can contact the surface simultaneously, the construction of a distal-end assembly for these catheters is complicated and costly.

Embodiments of the present invention that are described hereinafter provide an expandable flexible distal-end assembly configured for sensing and/or ablation comprising two flexible substrates, such as printed circuit boards (PCB), upon which an array of electrodes, together with conductors to the electrodes, are printed. The PCBs are attached (e.g., cemented) on either side of a flat flexible Nitinol backing sheet, within which irrigation channels are formed. The PCB/Nitinol combination may be formed with other elements, such as holes to permit blood flow.

While operating as sensing electrodes, once the distal-end assembly of the catheter has exited from a sheath, which is typically prepositioned in the heart chamber, one of the PCBs of the distal end may be pressed against heart chamber tissue so that its electrodes contact the tissue. The electrodes of the other PCB may be used for far-field acquisition.

In some embodiments, the set of electrodes in contact with tissue may be further used for ablation by switching the electrodes to an ablative power source, with the irrigation channels providing cooling. In one embodiment for IRE ablation, irrigation may be applied to cool electrode edges in order to avoid undesirable thermal effects such as charring or coagulum. In another embodiment, in an RF ablative mode, the irrigation is applied to cool the electrodes so as to maintain acceptable tissue temperature.

In one embodiment, the irrigation is performed by convection, by flowing a coolant (e.g., saline solution) into blood in the vicinity of the electrodes via openings (e.g., holes) in the PCBs connected to the channels. In another embodiment, the irrigation runs in the irrigation channels in a closed loop to cool the electrodes using heat conduction.

The disclosed flexible distal-end assemblies of catheters having double-sided electrode arrays may enable improved EP diagnostics and ablation with greater efficiency and accuracy and in a cost-effective manner.

System Description

FIG. 1 is a schematic, pictorial illustration of a catheter-based cardiac diagnostic and ablation system 20 comprising a double-sided electrode catheter 21, in accordance with an embodiment of the present invention. System 20 is used to determine the position of a flexible distal-end assembly 40 of catheter 21, seen in an inset 25 fitted at a distal end of a shaft 22, and subsequently to ablate a target cardiac tissue of a heart 26.

As seen in an inset 25, a flexible distal-end assembly 40 of shaft 22 of the catheter is inserted through a sheath 23 into heart 26 of a patient 28 lying on a table 29. The proximal end of catheter 21 is connected to a control console 24.

In the embodiment described herein, flexible distal-end assembly 40 carries, on one facet of the distal-end assembly, electrodes 50 for electrophysiological diagnostic purposes, such as sensing arrhythmia activity in tissue inside heart 26 and subsequent IRE ablation of the arrhythmogenic tissue. A similar electrode array is disposed on the opposing facet of flexible distal-end assembly 40 (shown on FIG. 2) and is used to acquire, in parallel, far-field electro-potentials. However, the two opposing facets may reverse functionally depending on which facet is deemed (e.g., by a system processor) to be in contact with tissue.

Expandable frames (e.g., of basket or balloon catheters) carrying diagnostic electrodes and far-field sensing electrodes are described in U.S. patent application Ser. No. 16/170,631 filed Oct. 25, 2018, titled "Electrodes On double-Sided Printed Circuit Board (PCB) To Cancel Far-Field Signal," which is assigned to the assignee of the present patent application, which document is incorporated by reference with a copy provided in the Appendix.

Physician 30 navigates distal-end assembly 40 of shaft 22 to a target location in heart 26 by manipulating shaft 22 using a manipulator 32 near the proximal end of the catheter and/or deflection from the sheath 23. During the insertion of shaft 22, distal-end assembly 40 is maintained in a collapsed or folded configuration by sheath 23. By containing distal-end assembly 40 in a collapsed or folded configuration, sheath 23 also serves to minimize vascular trauma along the way to target location.

To track positions of diagnostic electrodes 50, a plurality of external electrodes 27 is coupled to the body of patient 28; for example, three external electrodes 27 may be coupled to the patient's chest, and another three external electrodes may be coupled to the patient's back. (For ease of illustration, only one external electrode is shown in FIG. 1.) In some embodiments, electrodes 50 sense potentials induced in heart 26 by applying voltages between pairs of external electrodes 27.

A similar position tracking technique to the one described above, that can also be used for tracking the locations of diagnostic electrodes 50 inside heart 26, is described in U.S. patent application Ser. No. 15/966,514, filed Apr. 30, 2018, titled "Improved Active Voltage Location (AVL) Resolution," which is assigned to the assignee of the present patent application, which document is incorporated by reference with a copy provided in the Appendix.

Based on the potentials sensed by electrodes 50, and given the known positions of external electrodes 27 on the patient's body, a processor 41 calculates an estimated location of at least a portion of electrodes 50 within the patient's heart. Processor 41 may thus associate any given signal received from electrodes 50, such as an electrophysiological signal, with the location at which the signal was acquired.

Processor 41 is comprised in control console 24, and is typically a general-purpose computer, with suitable front end and interface circuits 38 for receiving signals from catheter 21, as well as for applying treatment via catheter 21 in heart 26 and for controlling the other components of system 20. Processor 41 typically comprises a general-purpose computer with software programmed to carry out the functions described herein. The software may be downloaded to the computer in electronic form, over a network, for example, or it may, alternatively or additionally, be provided and/or stored on non-transitory tangible media, such as magnetic, optical, or electronic memory.

In particular, processor 41 runs a dedicated algorithm that enables processor 41 to perform the disclosed steps, comprising calculations of the locations and respective proximities.

The example configuration shown in FIG. 1 is chosen purely for the sake of conceptual clarity. The disclosed techniques may similarly be applied using other system components and settings. For example, system 20 may comprise other components and perform non-cardiac diagnostics.

Flexible Distal-End Assembly for Double-Sided Electrode Array and Irrigation

Figure 2A:
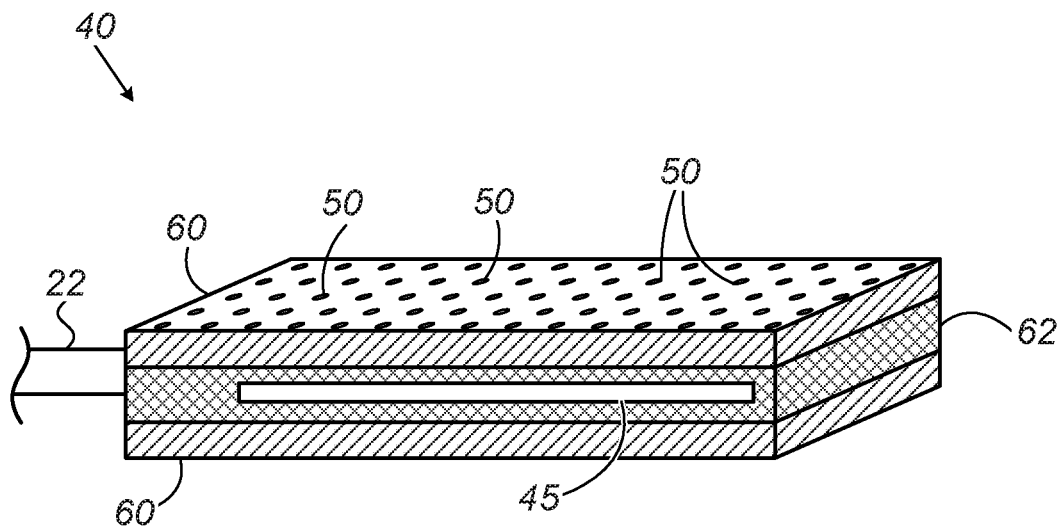
FIGS. 2A and 2B are isometric views of flexible distal-end assemblies of the double-sided electrode catheter of FIG. 1, including a cross-sectional view of the assembly layers with irrigation in closed loop and irrigation by convection, respectively, in accordance with embodiments of the present invention.
Figure 2B:
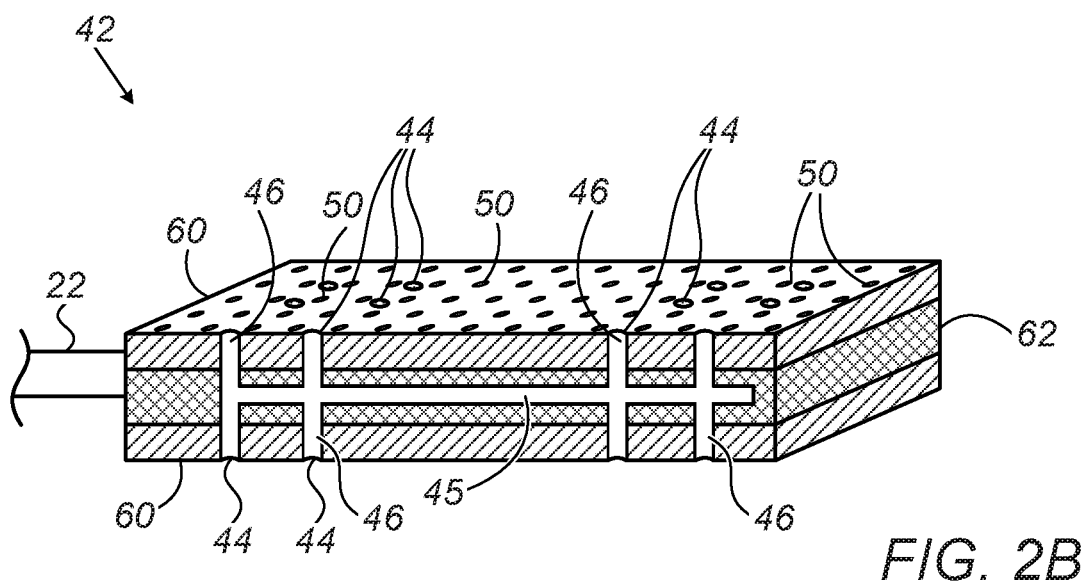

FIGS. 2A and 2B are isometric views of flexible distal-end assemblies 40 and 42 of double-sided electrode catheter 21 of FIG. 1, including a cross-sectional view of the assembly layers with irrigation in closed loop and irrigation by convection, respectively, in accordance with embodiments of the present invention. The shown embodiments depict only elements of the disclosed embodiments that enable the disclosed sensing and/or ablative functionalities. Therefore, additional elements, such as encapsulation of edges in soft material to avoid tissue injury, are not shown. Other features or devices that may be disposed on assemblies 40 and 42, such as temperature sensors, are omitted for clarity. Finally, the proportions of assemblies 40 and 42 are distorted in order to better view the cross-section, where in practice flexible distal-end assemblies 40 and 42 are typically far thinner compared to their length and width. An actual assembly 40 or 42 design will balance flexibility (e.g., level of conformity to an anatomy) with contact force of the electrode array.

As FIG. 2A shows, assembly 40 comprises two PCBs 50 upon which are printed arrays of electrodes 50. The electrodes are connected to conductors (e.g., wires or metal traces, neither shown) that are proximally connected to electrical wires (also not shown) passing in shaft 22. The PCBs are cemented on either side of a flat flexible Nitinol backing sheet 62, within which irrigation channels 45 are formed. The irrigation channels may be formed in various ways, either, for example, as bores surrounded entirely in Nitinol or as depressions in the Nitinol that are covered with one of the PCBs. The irrigation channels are typically connected to a tube running in shaft 22 (not shown).

As FIG. 2B shows, in assembly 42 irrigation is performed by convection, by flowing a coolant (e.g., saline solution) into blood in the vicinity of the electrodes via openings 44 in the PCBs connected to channels 45. That is, irrigation channel 45 are connected to the surface of PCBs 60 with vertical fluid passages 46 extending from the PCB 60 to the channel 45 (top and bottom surfaces).

The configurations of distal-end assemblies 40 and 42 shown in FIGS. 2A and 2B are example configurations, which are chosen purely for the sake of conceptual clarity. Any other suitable configuration can be used in alternative embodiments. In an example embodiment, each facet of assembly 50 comprises fifty electrodes 50 arranged in an array of 5-by-10 electrodes. The size of the array, in the expanded position, is 10-by-20 mm. The thickness of the assembly is on the order of 0.1 mm. In the collapsed position, within the sheath, distal-end assembly is typically rolled to assume a diameter of 3 mm. Alternatively, any other suitable sizes can be used. Moreover, the shape of distal-end assemblies 40 and 42 need not necessarily be rectangular. Other suitable shapes, e.g., round or elliptic, can also be used.

FIG. 3 is a flow chart that schematically illustrates a method for manufacturing flexible distal-end assembly 40 of FIG. 2A, in accordance with an embodiment of the present invention. The manufacturing process begins with printing electrodes 50 array on a flexible PCB, at an electrode printing step 70. At a cutting PCB step 72, the PCB is cut to fit the size of parts used for PCBs 60.

Next, at an electrical wiring step 74, electrodes 50 are wired. Alternatively or additionally, step 70 may include printing conductors to connect electrodes 50.

At a flat backing sheet manufacturing step 76, which can be performed in parallel to steps 70-74, a flat flexible backing sheet 62 comprising irrigation channels 45 is manufactured.

At an assembling step 78, the two PCB parts 60 are attached (e.g., cemented) to either side of the flat flexible backing sheet 62 to form the flexible distal-end assembly 40, as described above.

Finally, at a fitting step 80, flexible distal-end assembly 40 is fitted at a distal-end of shaft 22, including performing the required electrical and mechanical connections so that assembly 40 can be medically used as described in FIG. 1.

The example flow chart shown in FIG. 3 is chosen purely for the sake of conceptual clarity. Additional steps that may be included, such as polishing the edges or encapsulating them in soft material, are omitted for simplicity of presentation.

Although the embodiments described herein mainly address cardiac applications, the methods and systems described herein can also be used in other medical applications, such as in neurology, otolaryngology, and renal denervation.

It will be thus appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A medical probe, comprising:
    a shaft for insertion into a cavity of an organ of a patient; and
    an expandable flexible distal-end assembly, which is fitted at a distal-end of the shaft and comprises:
        a flat flexible backing sheet, comprising irrigation channels extending through the flat flexible backing sheet;
        a first flexible substrate disposed on a first side of the flat flexible backing sheet; and
        a second flexible substrate disposed on a second side of the flat flexible backing sheet, the first and second flexible substrates each comprising respective arrays of electrodes disposed thereon and comprising fluid passages extending therethrough perpendicular to the irrigation channels, the fluid passages extending from a first opening defined by the first flexible substrate on a first side of the expandable flexible distal-end assembly, through the irrigation channels, and to an opening defined by the second flexible substrate on a second side of the expandable flexible distal-end assembly opposite the first side.

2. The medical probe according to claim 1, wherein the irrigation channels are configured to be in fluid communication with surrounding blood.

3. The medical probe according to claim 2, wherein the first flexible substrate and the second flexible substrate have openings formed therein, for flowing coolant from the irrigation channels into the surrounding blood.

4. The medical probe according to claim 1, wherein the first flexible substrate and the second flexible substrate are printed circuit boards (PCBs).

5. The medical probe according to claim 1, wherein the flat flexible backing sheet comprises nitinol.

6. The medical probe according to claim 1, wherein the distal-end assembly is rectangular.

* * * * *